(12) United States Patent
Bedingham et al.

(10) Patent No.: US 7,767,937 B2
(45) Date of Patent: *Aug. 3, 2010

(54) MODULAR SAMPLE PROCESSING KITS AND MODULES

(75) Inventors: William Bedingham, Woodbury, MN (US); Barry W. Robole, Woodville, WI (US)

(73) Assignee: 3M Innovative Properties Company, St. Paul, MN (US)

( * ) Notice: Subject to any disclaimer, the term of this patent is extended or adjusted under 35 U.S.C. 154(b) by 151 days.

This patent is subject to a terminal disclaimer.

(21) Appl. No.: 11/930,628

(22) Filed: Oct. 31, 2007

(65) Prior Publication Data
US 2008/0050276 A1 Feb. 28, 2008

Related U.S. Application Data

(63) Continuation of application No. 11/174,756, filed on Jul. 5, 2005, now Pat. No. 7,323,660.

(51) Int. Cl.
*F27B 9/16* (2006.01)
*F27B 9/36* (2006.01)
*G01N 35/04* (2006.01)
*C12Q 1/34* (2006.01)

(52) U.S. Cl. .................. 219/388; 219/428; 219/432; 435/288.4; 422/64; 422/72

(58) Field of Classification Search ............... None
See application file for complete search history.

(56) References Cited

U.S. PATENT DOCUMENTS 3,555,284 A 1/1971 Anderson (Continued)

FOREIGN PATENT DOCUMENTS

CA 2 130 013 3/1999

(Continued)

OTHER PUBLICATIONS

Sambrook et al., Molecular Cloning, A laboratory Manual, 2nd Edition, Cold Spring Harbor Laboratory, 1989 (30 pgs) includes Title and copyright pages and Table to Contents.

(Continued)

*Primary Examiner*—Joseph M Pelham
(74) *Attorney, Agent, or Firm*—Nicole J. Einerson (57) ABSTRACT

Modular sample processing apparatus kits that can provide a user with the flexibility to customize a disk-based assay in view of a variety of factors are disclosed. The sample processing apparatus kits of the present invention include one or more process modules that can be retained within openings in a frame. The frame and process modules of the sample processing apparatus kits are preferably adapted for use in sample processing systems that compress the apparatus. The process modules may contain different reagents to perform different tests on the same sample materials or a variety of sample materials. As a result, a single sample processing apparatus can be used to perform a variety of different tests and may include a quality control module capable of providing feedback to the user as to the accuracy of the processes run using the sample processing apparatus. Methods of using the sample processing apparatus that include deforming the process modules and frame are also disclosed.

22 Claims, 4 Drawing Sheets

U.S. PATENT DOCUMENTS

| | | |
|---|---|---|
| 3,795,451 A | 3/1974 | Mailen |
| 3,798,459 A | 3/1974 | Anderson et al. |
| 3,856,470 A | 12/1974 | Cullis et al. |
| 3,873,217 A | 3/1975 | Anderson et al. |
| 3,912,799 A | 10/1975 | Chisholm |
| 3,964,867 A | 6/1976 | Berry |
| 4,030,834 A | 6/1977 | Bauer et al. |
| 4,111,304 A | 9/1978 | Lucas |
| 4,123,173 A | 10/1978 | Bullock et al. |
| 4,244,916 A | 1/1981 | Guigan |
| 4,252,538 A | 2/1981 | Barr |
| 4,256,696 A | 3/1981 | Soodak |
| 4,384,193 A | 5/1983 | Kledzik et al. |
| 4,390,499 A | 6/1983 | Curtis et al. |
| 4,396,579 A | 8/1983 | Schroeder et al. |
| D271,993 S | 12/1983 | Swartz |
| 4,456,581 A | 6/1984 | Edelmann et al. |
| D274,553 S | 7/1984 | Perry |
| 4,476,733 A | 10/1984 | Chlosta et al. |
| 4,488,810 A | 12/1984 | Hatanaka et al. |
| 4,498,896 A | 2/1985 | Leis |
| D277,891 S | 3/1985 | Uffenheimer et al. |
| 4,554,436 A | 11/1985 | Chlosta et al. |
| 4,580,896 A | 4/1986 | Brickus et al. |
| 4,632,908 A | 12/1986 | Schultz |
| D288,124 S | 2/1987 | Brickus et al. |
| 4,673,657 A | 6/1987 | Christian |
| 4,695,430 A | 9/1987 | Coville et al. |
| 4,814,279 A * | 3/1989 | Sugaya .................... 435/303.1 |
| 4,839,296 A | 6/1989 | Kennedy et al. ............ 436/170 |
| 4,906,432 A | 3/1990 | Geiselman .................. 422/63 |
| 4,933,146 A | 6/1990 | Meyer et al. |
| 4,981,801 A | 1/1991 | Suzuki et al. |
| 5,049,591 A | 9/1991 | Hayashi et al. ............. 521/159 |
| 5,079,155 A | 1/1992 | Cox et al. .................. 435/181 |
| 5,086,337 A | 2/1992 | Noro et al. .................... 357/79 |
| 5,128,197 A | 7/1992 | Kobayashi et al. .......... 428/225 |
| 5,135,786 A | 8/1992 | Hayashi et al. ............ 428/35.5 |
| 5,139,832 A | 8/1992 | Hayashi et al. ............ 428/35.5 |
| D329,024 S | 9/1992 | Marks |
| 5,145,935 A | 9/1992 | Hayashi ....................... 528/65 |
| 5,154,888 A | 10/1992 | Zander et al. |
| 5,182,083 A | 1/1993 | Barker et al. .................. 422/63 |
| 5,207,987 A | 5/1993 | Kureshy et al. |
| 5,219,526 A | 6/1993 | Long |
| 5,229,297 A | 7/1993 | Schnipelsky et al. |
| 5,254,479 A | 10/1993 | Chemelli |
| 5,258,163 A | 11/1993 | Krause et al. |
| 5,264,184 A | 11/1993 | Aysta et al. ................. 422/101 |
| 5,278,377 A | 1/1994 | Tsai |
| 5,288,463 A | 2/1994 | Chemelli |
| 5,310,523 A | 5/1994 | Smethers et al. |
| 5,336,467 A | 8/1994 | Heidt et al. |
| 5,411,065 A | 5/1995 | Meador et al. .................. 141/1 |
| 5,415,839 A | 5/1995 | Zaun et al. |
| 5,422,271 A | 6/1995 | Chen et al. |
| 5,429,810 A | 7/1995 | Knaepler et al. ............. 422/300 |
| 5,438,128 A | 8/1995 | Nieuwkerk et al. ........ 536/25.4 |
| 5,439,649 A | 8/1995 | Tseung et al. |
| 5,446,270 A | 8/1995 | Chamberlain et al. |
| 5,461,134 A | 10/1995 | Leir et al. |
| 5,464,541 A | 11/1995 | Aysta et al. ................. 210/767 |
| 5,496,518 A | 3/1996 | Arai et al. ...................... 422/64 |
| 5,496,520 A | 3/1996 | Kelton et al. |
| 5,527,931 A | 6/1996 | Rich et al. |
| 5,529,708 A | 6/1996 | Palmgren et al. |
| 5,571,410 A | 11/1996 | Swedberg et al. ........ 210/198.2 |
| 5,587,128 A | 12/1996 | Wilding et al. |
| 5,593,838 A | 1/1997 | Zanzucchi et al. ............. 435/6 |
| 5,599,501 A | 2/1997 | Carey et al. |
| 5,601,141 A | 2/1997 | Gordon et al. |
| 5,604,130 A | 2/1997 | Warner et al. |
| 5,616,301 A | 4/1997 | Moser et al. |
| 5,637,469 A | 6/1997 | Wilding et al. ............. 435/7.21 |
| 5,639,428 A | 6/1997 | Cottingham |
| 5,639,810 A | 6/1997 | Smith, III et al. ........... 524/269 |
| 5,691,208 A | 11/1997 | Miltenyi et al. ............. 436/526 |
| RE35,716 E | 1/1998 | Stapleton et al. |
| 5,720,923 A | 2/1998 | Haff et al. |
| 5,721,123 A | 2/1998 | Hayes et al. |
| 5,726,026 A | 3/1998 | Wilding et al. |
| 5,792,372 A | 8/1998 | Brown et al. |
| 5,795,547 A | 8/1998 | Moser et al. |
| 5,800,785 A | 9/1998 | Bochner |
| 5,804,141 A | 9/1998 | Chianese |
| 5,811,296 A | 9/1998 | Chemelli et al. |
| 5,819,842 A | 10/1998 | Potter et al. |
| 5,822,903 A | 10/1998 | Davis, Sr. .................. 42/69.01 |
| 5,833,923 A | 11/1998 | McClintock et al. |
| 5,863,502 A | 1/1999 | Southgate et al. |
| 5,863,801 A | 1/1999 | Southgate et al. |
| 5,869,002 A | 2/1999 | Limon et al. |
| 5,876,675 A | 3/1999 | Kennedy |
| 5,886,863 A | 3/1999 | Nagasaki et al. |
| 5,922,617 A | 7/1999 | Wang et al. |
| 5,925,455 A | 7/1999 | Bruzzone et al. |
| 5,948,227 A | 9/1999 | Dubrow ...................... 204/455 |
| 5,976,468 A | 11/1999 | Godec et al. ................. 422/100 |
| 5,997,818 A | 12/1999 | Hacker et al. .............. 422/68.1 |
| 6,001,643 A | 12/1999 | Spaulding ................... 435/298 |
| 6,007,690 A | 12/1999 | Nelson et al. .............. 204/601 |
| 6,007,914 A | 12/1999 | Joseph et al. |
| 6,013,513 A | 1/2000 | Reber et al. |
| 6,030,581 A | 2/2000 | Virtanen |
| 6,048,457 A | 4/2000 | Kopaciewicz et al. .... 210/321.6 |
| 6,063,589 A | 5/2000 | Kellogg et al. |
| 6,068,751 A | 5/2000 | Neukermans ............... 204/601 |
| 6,074,827 A | 6/2000 | Nelson et al. .................. 435/6 |
| 6,093,370 A | 7/2000 | Yasuda et al. |
| 6,103,199 A | 8/2000 | Bjornson et al. ............ 422/100 |
| 6,143,247 A | 11/2000 | Sheppard, Jr. et al. ......... 422/63 |
| 6,143,248 A | 11/2000 | Kellogg et al. |
| 6,153,012 A | 11/2000 | Rupp et al. |
| 6,168,759 B1 | 1/2001 | Green et al. |
| 6,168,948 B1 | 1/2001 | Anderson et al. ........ 435/287.2 |
| 6,183,693 B1 | 2/2001 | Bogen et al. |
| 6,184,029 B1 | 2/2001 | Wilding et al. |
| 6,190,617 B1 | 2/2001 | Clark et al. |
| 6,197,595 B1 | 3/2001 | Anderson et al. ........... 436/180 |
| 6,200,474 B1 | 3/2001 | Kopaciewicz et al. .... 210/321.6 |
| D441,873 S | 5/2001 | Kohler |
| 6,265,168 B1 | 7/2001 | Gjerde et al. ................... 435/6 |
| 6,284,113 B1 | 9/2001 | Bjornson et al. ............ 204/453 |
| 6,296,809 B1 | 10/2001 | Richards et al. |
| 6,302,134 B1 | 10/2001 | Kellogg et al. ................ 137/74 |
| 6,306,273 B1 | 10/2001 | Wainright et al. ........... 204/454 |
| 6,319,469 B1 | 11/2001 | Mian et al. |
| 6,344,326 B1 | 2/2002 | Nelson et al. .................. 435/6 |
| 6,375,898 B1 | 4/2002 | Ulrich et al. |
| 6,391,264 B2 | 5/2002 | Hammer et al. |
| 6,399,025 B1 | 6/2002 | Chow |
| 6,413,782 B1 | 7/2002 | Parce et al. |
| 6,432,365 B1 | 8/2002 | Levin et al. |
| 6,440,725 B1 | 8/2002 | Pourahmadi et al. ...... 435/288.5 |
| 6,450,047 B2 | 9/2002 | Swedberg et al. ............. 73/863 |
| 6,451,260 B1 | 9/2002 | Düsterhöft et al. ......... 422/68.1 |
| 6,461,287 B1 | 10/2002 | Glater |
| 6,465,225 B1 | 10/2002 | Fuhr et al. ................. 435/173.1 |
| 6,467,275 B1 | 10/2002 | Ghoshal |
| 6,479,300 B1 | 11/2002 | Jiang et al. .................. 436/518 |
| 6,527,432 B2 | 3/2003 | Kellogg et al. |
| 6,532,997 B1 | 3/2003 | Bedingham et al. ............ 141/1 |
| 6,548,788 B2 | 4/2003 | Kellogg et al. ............... 219/543 |
| 6,558,947 B1 | 5/2003 | Lund et al. |

| | | |
|---|---|---|
| 6,565,808 B2 | 5/2003 | Hudak et al. ............... 422/58 |
| 6,566,637 B1 | 5/2003 | Reverz et al. |
| 6,572,830 B1 | 6/2003 | Burdon et al. |
| 6,582,662 B1 | 6/2003 | Kellogg et al. |
| 6,593,143 B1 | 7/2003 | Gordon |
| 6,617,136 B2 | 9/2003 | Parthasarathy et al. |
| 6,627,159 B1 | 9/2003 | Bedingham et al. |
| 6,632,399 B1 | 10/2003 | Kellogg et al. ............. 422/72 |
| 6,645,758 B1 | 11/2003 | Schnipelsky et al. |
| 6,648,853 B1 | 11/2003 | McEntee .................. 604/88 |
| 6,660,147 B1 | 12/2003 | Woudenberg et al. |
| 6,664,104 B2 | 12/2003 | Pourahmadi et al. ..... 435/288.6 |
| 6,692,596 B2 | 2/2004 | Moll et al. .............. 156/73.1 |
| 6,720,187 B2 | 4/2004 | Bedingham et al. ........... 436/45 |
| 6,723,236 B2 | 4/2004 | Fisk et al. ............... 210/198.2 |
| 6,730,516 B2 | 5/2004 | Jedrzejewski et al. ........ 436/43 |
| 6,734,401 B2 | 5/2004 | Bedingham et al. |
| 6,780,818 B2 | 8/2004 | Gundel et al. ............. 502/402 |
| 6,814,935 B2 | 11/2004 | Harms et al. |
| 6,824,738 B1 | 11/2004 | Neeper et al. ............... 422/72 |
| 6,889,468 B2 | 5/2005 | Bedingham et al. |
| 6,987,253 B2 | 1/2006 | Bedingham et al. |
| 7,026,168 B2 | 4/2006 | Bedingham et al. |
| 7,164,107 B2 | 1/2007 | Bedingham et al. ......... 219/752 |
| 7,192,560 B2 | 3/2007 | Parthasarathy et al. ...... 422/101 |
| 7,273,591 B2 * | 9/2007 | Sellers et al. ............... 422/104 |
| 7,322,254 B2 | 1/2008 | Bedingham et al. ........... 73/863 |
| 7,323,660 B2 | 1/2008 | Bedingham et al. |
| D564,667 S | 3/2008 | Bedingham et al. |
| 7,396,508 B1 | 7/2008 | Richards et al. |
| 7,569,186 B2 | 8/2009 | Bedingham et al. |
| 2001/0045000 A1 | 11/2001 | Gundel et al. ............... 29/458 |
| 2002/0047003 A1 | 4/2002 | Bedingham et al. |
| 2002/0048533 A1 | 4/2002 | Bedingham et al. |
| 2002/0064885 A1 | 5/2002 | Bedingham et al. |
| 2003/0013203 A1 | 1/2003 | Jedrzejewski et al. ....... 436/102 |
| 2003/0017567 A1 | 1/2003 | Parthasarathy et al. ...... 435/194 |
| 2003/0044322 A1 | 3/2003 | Andersson et al. .......... 422/100 |
| 2003/0053934 A1 | 3/2003 | Andersson et al. ........... 422/72 |
| 2003/0118804 A1 | 6/2003 | Bedingham et al. ....... 428/301.4 |
| 2003/0120062 A1 | 6/2003 | Parthasarathy et al. ..... 536/25.4 |
| 2003/0124506 A1 | 7/2003 | Bedingham et al. |
| 2003/0138779 A1 | 7/2003 | Parthasarathy et al. |
| 2003/0139550 A1 | 7/2003 | Savu et al. ................ 526/243 |
| 2003/0152491 A1 | 8/2003 | Kellogg et al. ............... 422/99 |
| 2003/0152994 A1 | 8/2003 | Woudenberg et al. |
| 2003/0155034 A1 | 8/2003 | De Beukeleer et al. ...... 141/130 |
| 2003/0228706 A1 | 12/2003 | Ramstad et al. ............. 436/178 |
| 2003/0231878 A1 | 12/2003 | Shigeura |
| 2004/0016702 A1 | 1/2004 | Hennessy et al. ........... 210/660 |
| 2004/0016898 A1 | 1/2004 | Cox et al. |
| 2004/0018116 A1 | 1/2004 | Desmond et al. ............. 422/58 |
| 2004/0018117 A1 | 1/2004 | Desmond et al. |
| 2004/0023371 A1 | 2/2004 | Fawcett |
| 2004/0121471 A1 | 6/2004 | Dufresne et al. |
| 2004/0179974 A1 | 9/2004 | Bedingham et al. ......... 422/100 |
| 2004/0209258 A1 | 10/2004 | Parthasarathy et al. ......... 435/6 |
| 2005/0036906 A1 | 2/2005 | Sellers et al. |
| 2005/0130177 A1 | 6/2005 | Bedingham et al. |
| 2005/0142563 A1 | 6/2005 | Haddad et al. ................. 435/6 |
| 2005/0142570 A1 | 6/2005 | Parthasarathy et al. .......... 435/6 |
| 2005/0142571 A1 | 6/2005 | Parthasarathy et al. .......... 435/6 |
| 2005/0142663 A1 | 6/2005 | Parthasarathy et al. ...... 436/174 |
| 2005/0180890 A1 | 8/2005 | Bedingham et al. |
| 2006/0013732 A1 | 1/2006 | Parthasarathy et al. ..... 422/68.1 |
| 2006/0269451 A1 | 11/2006 | Bedingham et al. |
| 2007/0007270 A1 | 1/2007 | Bedingham et al. |
| 2007/0009391 A1 | 1/2007 | Bedingham et al. |
| 2007/0010007 A1 | 1/2007 | Aysta et al. |
| 2007/0114229 A1 | 5/2007 | Bedingham et al. |
| 2007/0142780 A1 | 6/2007 | Van Lue .................... 604/167 |

FOREIGN PATENT DOCUMENTS

| | | |
|---|---|---|
| DE | 3712624 | 11/1988 |
| EP | 0 169 306 A2 | 1/1986 |
| EP | 0 281 368 | 9/1988 |
| EP | 0 169 306 B1 | 5/1990 |
| EP | 0 402 994 A2 | 12/1990 |
| EP | 0 402 994 B1 | 11/1994 |
| EP | 0 693 560 A2 | 1/1996 |
| EP | 0 810 030 A1 | 12/1997 |
| EP | 0 965 388 | 12/1999 |
| EP | 1 010 979 A1 | 6/2000 |
| EP | 0 807 486 B1 | 12/2001 |
| EP | 0 810 030 B1 | 3/2003 |
| EP | 1 010 979 B1 | 10/2003 |
| JP | 9-72912 | 3/1997 |
| JP | 11124419 | 5/1999 |
| WO | WO 91/19567 A1 | 12/1991 |
| WO | WO 94/26414 A1 | 11/1994 |
| WO | WO 94/29400 A1 | 12/1994 |
| WO | WO 95/18676 A1 | 7/1995 |
| WO | WO 95/19781 | 7/1995 |
| WO | WO 96/15576 A1 | 5/1996 |
| WO | WO 96/34028 A1 | 10/1996 |
| WO | WO 96/34029 A1 | 10/1996 |
| WO | WO 96/35458 A2 | 11/1996 |
| WO | WO 96/41864 A1 | 12/1996 |
| WO | WO 97/00230 | 1/1997 |
| WO | WO 97/19567 A1 | 5/1997 |
| WO | WO 97/21090 A1 | 6/1997 |
| WO | WO 97/46707 A2 | 12/1997 |
| WO | WO 97/46707 A3 | 12/1997 |
| WO | WO 98/04909 | 2/1998 |
| WO | WO 98/07019 A1 | 2/1998 |
| WO | WO 98/49340 A1 | 11/1998 |
| WO | WO 98/50147 A1 | 11/1998 |
| WO | WO 98/53311 A2 | 11/1998 |
| WO | WO 99/09394 A1 | 2/1999 |
| WO | WO 99/15876 | 4/1999 |
| WO | WO 99/15888 | 4/1999 |
| WO | WO 99/40174 | 8/1999 |
| WO | WO 99/44740 A1 | 9/1999 |
| WO | WO 99/46591 | 9/1999 |
| WO | WO 99/55827 A1 | 11/1999 |
| WO | WO 99/58245 A1 | 11/1999 |
| WO | WO 99/67639 A1 | 12/1999 |
| WO | WO 00/05582 A2 | 2/2000 |
| WO | WO 00/40750 A1 | 7/2000 |
| WO | WO 00/45180 | 8/2000 |
| WO | WO 00/50172 A1 | 8/2000 |
| WO | WO 00/50642 A1 | 8/2000 |
| WO | WO 00/62051 | 10/2000 |
| WO | WO 00/68336 A1 | 11/2000 |
| WO | WO 00/69560 A1 | 11/2000 |
| WO | WO 00/78455 A1 | 12/2000 |
| WO | WO 00/79285 A2 | 12/2000 |
| WO | WO 01/07892 A1 | 2/2001 |
| WO | WO 01/12327 | 2/2001 |
| WO | WO 01/30995 | 5/2001 |
| WO | WO 01/38865 | 5/2001 |
| WO | WO 03/054509 | 7/2003 |
| WO | WO 03/054510 | 7/2003 |
| WO | WO 03/058224 | 7/2003 |
| WO | WO 03/058253 A1 | 7/2003 |
| WO | WO 03/104783 A1 | 12/2003 |
| WO | WO 2004/010760 | 2/2004 |
| WO | WO 2004/011142 | 2/2004 |
| WO | WO 2004/011143 A2 | 2/2004 |
| WO | WO 2004/011147 A1 | 2/2004 |
| WO | WO 2004/011148 A2 | 2/2004 |
| WO | WO 2004/011149 A1 | 2/2004 |

| WO | WO 2004/011365 A2 | 2/2004 |
| WO | WO 2004/011592 A2 | 2/2004 |
| WO | WO 2004/011681 A1 | 2/2004 |
| WO | WO 2004/094672 | 11/2004 |
| WO | WO 2005/005045 A1 | 1/2005 |
| WO | WO 2005/016532 A2 | 2/2005 |
| WO | WO 2005/016532 A3 | 2/2005 |

OTHER PUBLICATIONS

Emmer, A. et al.; "Wall deactivation with fluorosurfactants for capillary electrophoretic analysis of biomolecules"; Electrophoresis 2001, 22; pp. 660-665.

Garcia, A. et al.; "Comparison of Two Leukocyte Extraction Methods for Cytomegalovirus Antigenemia Assay"; Journal of Clinical Microbiology, Jan. 1996; vol. 34, No. 1; pp. 182-184.

*Handbook of Pressure Sensitive Adhesive Technology*, Donatas Satas (Ed.) $2^{nd}$ Edition, Title page, Publication page, Table of Contents, and p. 172, and Fig. 8-16 on p. 173, Van Nostrand Reinhold, New York, NY 1989.

*Handbook of Pressure Sensitive Adhesive Technology*, $3^{rd}$ Edition, Title page, Publication page, Table of Contents, and pp. 508-517.

Litton Product Brochure; Poly Scientific EC3848 High Speed Slip Ring Capsule; Blacksburg, VA; 2 pgs (Oct. 1999).

Meridian Laboratory Datasheet [online]; Rotocon high performance rotary electrical contacts; 5 pgs [retrieved on Jun. 18, 2002]. Retrieved from the Internet: <http://www.meridianlab.com/>.

Meridian Laboratory Datasheet [online]: Model MM Micro-Minature; 5 pgs. [retrieved on Jul. 19, 2001]. Retrieved from the Internet: <http://www.meridianlab.com/mm.htm>.

Motion Technology Product Guide; Commercial and Military/Aerospace Applications; Blacksburg, VA; 8 pgs. (Jul. 1999).

NIST Grant, Project Brief [online]; "Tools for DNA Diagnostics (Oct. 1998) Integrated, Micro-Sample Preparation System for Genetic Analysis," [retrieved on Aug. 5, 2002] 2 pgs. Retrieved form the internet at <http://jazz.nist.gov/atpcf/prjbriefs/prjbrief.cfm?ProjectNumber=98/08/0031>.

*Test Methods for Pressure Sensitive Adhesive Tapes*, Pressure Sensitive Tape Council, (1996) (4 pgs).

\* cited by examiner

MODULAR SAMPLE PROCESSING KITS AND MODULES

CROSS REFERENCE TO RELATED APPLICATIONS

This application is a continuation of U.S. application Ser. No. 11/174,756, filed Jul. 5, 2005 now U.S. Pat. No. 7,323,660, now Allowed, the disclosure of which is incorporated by reference in its entirety herein.

BACKGROUND OF THE INVENTION

The present invention relates to modular sample processing apparatus kit that can be used to process samples that may contain one or more analytes of interest.

Many different chemical, biochemical, and other reactions are sensitive to temperature variations. Examples of thermal processes in the area of genetic amplification include, but are not limited to, Polymerase Chain Reaction (PCR), Sanger sequencing, etc. The reactions may be enhanced or inhibited based on the temperatures of the materials involved. Although it may be possible to process samples individually and obtain accurate sample-to-sample results, individual processing can be time-consuming and expensive.

A variety of sample processing devices and apparatus have been developed to process samples quickly and efficiently. Examples of some particularly useful sample processing devices may be found in, e.g., commonly-assigned U.S. Pat. No. 6,734,401 titled ENHANCED SAMPLE PROCESSING DEVICES SYSTEMS AND METHODS (Bedingham et al.).

Although these sample processing devices are useful, in many instances they provide significantly larger numbers of process chambers (e.g., 96, 384 or more process chambers) than needed for a particular assay (in which as few as one process chamber and associated reagents may be needed). Furthermore, many of these sample processing devices contain reagents that are by far the most costly component of the sample processing device. As a result, using only a portion of the process chambers and the reagents contained in a sample processing device can be prohibitively expensive.

SUMMARY OF THE INVENTION

The present invention provides modular sample processing apparatus kits that can provide a user with the flexibility to customize a disk-based assay in view of a variety of factors. Generally, the sample processing apparatus kits of the present invention include one or more process modules that can be retained within openings in a frame.

The frame and process modules of the sample processing apparatus kits are preferably adapted for use in sample processing systems that compress the apparatus such as, e.g., the compression systems described in, e.g., U.S. patent application Ser. No. 11/174,757, titled SAMPLE PROCESSING DEVICE COMPRESSION SYSTEMS AND METHODS, filed on even date herewith.

Among the potential advantages of the present invention is the ability of the customer to assemble different process modules within the frame of a sample processing apparatus of the present invention. The different process modules may contain different reagents to perform different tests on the same sample materials or a variety of sample materials. As a result, a single sample processing apparatus can be used to perform a variety of different tests and may include a quality control module capable of providing feedback to the user as to the accuracy of the processes run using the sample processing apparatus.

Furthermore, only process modules that are needed may be used, offering potentially significant savings for the user—especially if the process modules are preprinted with expensive reagents that would otherwise be wasted if provided in a conventional device. If fewer process modules are needed than a given frame can contain, the remainder of the openings in the frame may be loaded with blank process modules to provide a complete apparatus for processing if needed for proper processing in a given system (such as the systems described in U.S. patent application Ser. No. 11/174,757, titled SAMPLE PROCESSING DEVICE COMPRESSION SYSTEMS AND METHODS, filed on even date herewith.

Although described herein as "kits", the process modules and frames may be provided to users either assembled or not. In some instances, the kits may include a one or more blank modules for use as described herein.

Another potential advantage of some of the sample processing apparatus of the present invention may include, e.g., process chambers arranged in a compliant annular processing ring that is adapted to conform to the shape of an underlying thermal transfer surface under pressure. That compliance may be delivered in the apparatus of the present invention by, e.g., locating the process chambers in an annular processing ring in which a majority of the volume is occupied by the process chambers which are preferably formed by voids extending through the bodies of the process modules in the apparatus. In such a construction, limited amounts of the body forming the structure of the modules is present within the annular processing ring, resulting in improved flexibility of the apparatus within the annular processing ring.

Other optional features that may improve compliance within the annular processing ring may include a composite structure within the annular processing ring that includes covers attached to a process module body using pressure sensitive adhesive that exhibits viscoelastic properties. The viscoelastic properties of pressure sensitive adhesives may allow for relative movement of the covers and process module bodies during deformation or thermal expansion/contraction while maintaining fluidic integrity of the fluid structures in the sample processing apparatus of the present invention.

The use of covers attached to a process module body as described in connection with the sample processing apparatus of the present invention may also provide advantages in that the properties of the materials for the different covers and process module bodies may be selected to enhance performance of the apparatus.

For example, some of the covers may preferably be constructed of relatively inextensible materials to resist bulging or deformation in response forces generated by the sample materials within the process chambers and/or other features of any fluid structures. Those forces may be significant where, e.g., the sample processing apparatus is rotated to deliver and/or process sample materials in the process chambers. Examples of some materials that may be relatively inextensible may include, e.g., polyesters, metal foils, polycarbonates, etc. It should, however, be understood that inextensibility may not necessarily be required. For example, in some embodiments, one or more covers may be selected because they provide for some extensibility.

Another property that may preferably be exhibited by some of the covers used in connection with the present invention is thermal conductivity. Using materials for the covers that enhance thermal conductivity may improve thermal performance where, e.g., the temperature of the sample materials in the process chambers are preferably heated or cooled rapidly to selected temperatures or where accurate temperature control is desirable. Examples of materials that may provide desirable thermal conductive properties may include, e.g., metallic layers (e.g., metallic foils), thin polymeric layers, etc.

Another potentially useful property in the covers used in connection with the present invention may be their ability to transmit electromagnetic energy of selected wavelengths. For example, in some apparatus, electromagnetic energy may be delivered into the process chambers to heat materials, excite materials (that may, e.g., fluoresce, etc.), visually monitor the materials in the process chamber, etc.

As discussed above, if the materials used for the covers are too extensible, they may bulge or otherwise distort at undesirable levels during, e.g., rotation of the disk, heating of materials within the process chambers, etc. One potentially desirable combination of properties in the covers used to construct process chambers of the present invention may include relative inextensibility, transmissivity to electromagnetic energy of selected wavelengths, and thermal conductivity. Where each process chamber is constructed by a void in the process module body and a pair of covers on each side of the body, one cover may be selected to provide the desired transmissivity and inextensibility while the other cover may be selected to provide thermal conductivity and inextensibility. One suitable combination of covers may include, e.g., a polyester cover that provides transmissivity and relative inextensibility and a metallic foil cover that provides thermal conductivity and inextensibility on the opposite side of the process chamber. Using pressure sensitive adhesive to attach relatively inextensible covers to the process module bodies may preferably improve compliance and flexibility by allowing relative movement between the covers and the process module body that may not be present in other constructions.

The sample processing apparatus of the present invention are designed for processing sample materials that include chemical and/or biological mixtures with at least a portion being in the form of a liquid component. If the sample materials include a biological mixture, the biological mixture may preferably include biological material such as peptide- and/or nucleotide-containing material. It may further be preferred that the biological mixture include a nucleic acid amplification reaction mixture (e.g., a PCR reaction mixture or a nucleic acid sequencing reaction mixture).

Further, the fluid structures (if any) may preferably be unvented, such that the only opening into or out of the fluid structure is located proximate the input well into which the sample materials are introduced. In an unvented fluid structure, the terminal end, i.e., the portion distal from the axis of rotation and/or the input well, is sealed to prevent the exit of fluids from the process chamber.

In one aspect, the present invention provides a modular sample processing apparatus kit that includes a frame with a plurality of openings arranged in an annular array around a center of the frame and one or more process modules adapted to be retained within one opening of the plurality of openings in the frame. Adjacent process modules loaded into adjacent openings are separated from each other by a radial strut of the frame. Each process module includes a module body with first and second major surfaces; a metallic foil layer attached to the second major surface of the module body; a fluid structure in the process module, the fluid structure including an input well in fluid communication with a process chamber, wherein the input well is located radially inward of the process chamber relative to the center of the frame. The process chamber includes a volume defined by a void formed through the first and second major surfaces of the module body and the metallic foil layer attached to the second major surface over the void in the second major surface. The process chambers of the one or more process modules define an annular processing ring of the modular sample processing apparatus when the one or more process modules are retained within the plurality of openings in the frame. Each process module has a z-axis thickness measured in a direction normal to the first and second major surfaces of the module body that is larger than a z-axis thickness of the portion of each radial strut of the frame located within the annular processing ring.

In another aspect, the present invention provides a process module adapted for use in a modular sample processing apparatus having a frame with a plurality of openings arranged in an annular array around a center of the frame, the openings separated from each other by a radial strut. The process module includes a module body with first and second major surfaces; a metallic foil layer attached to the second major surface of the module body; a fluid structure in the process module, the fluid structure including an input well in fluid communication with a process chamber, wherein the input well is located radially inward of the process chamber relative to the center of the frame. The process chamber has a volume defined by a void formed through the first and second major surfaces of the module body and the metallic foil layer attached to the second major surface over the void in the second major surface. The process module has a z-axis thickness measured in a direction normal to the first and second major surfaces of the module body that is larger than a z-axis thickness of the portion of each radial strut of the frame located within the annular processing ring.

In another aspect, the present invention provides a method of processing sample materials, the method including providing a modular sample processing apparatus that includes a frame with a plurality of openings arranged in an annular array around a center of the frame and one or more process modules adapted to be retained within one opening of the plurality of openings in the frame, wherein adjacent process modules loaded into adjacent openings are separated from each other by a radial strut of the frame. Each process module further includes a module body with first and second major surfaces, a metallic foil layer attached to the second major surface of the module body, at least one process chamber with a volume defined by a void formed through the first and second major surfaces of the module body and the metallic foil layer attached to the second major surface over the void in the second major surface. The process chambers of the one or more process modules define an annular processing ring of the modular sample processing apparatus when the one or more process modules are retained within the plurality of openings in the frame. The method further includes providing sample material in the at least one process chamber of the one or more process modules and deforming the annular processing ring of the sample processing apparatus on a convex transfer surface of a thermal structure, wherein a portion of the one or more process modules and the frame are deflected to conform to the convex transfer surface. The sample processing apparatus is rotated about an axis of rotation while deforming the annular processing ring on the convex transfer surface.

These and other features and advantages of the present invention may be discussed below in connection with various exemplary embodiments of the invention.

DESCRIPTION OF EXEMPLARY EMBODIMENTS OF THE INVENTION

In the following description of exemplary embodiments of the invention, reference is made to the accompanying figures of the drawing which form a part hereof, and in which are shown, by way of illustration, specific embodiments in which the invention may be practiced. It is to be understood that other embodiments may be utilized and structural changes may be made without departing from the scope of the present invention.

The present invention provides modular sample processing apparatus kits and methods for using them that involve thermal processing, e.g., sensitive chemical processes such as PCR amplification, ligase chain reaction (LCR), self-sustaining sequence replication, enzyme kinetic studies, homogeneous ligand binding assays, and more complex biochemical or other processes that require precise thermal control and/or rapid thermal variations. The modular sample processing apparatus kits (when assembled) are preferably capable of being rotated while the temperature of sample materials in process chambers in the apparatus is being controlled.

Some examples of suitable construction techniques/materials that may be adapted for use in connection with the process modules of the present invention may be described in, e.g., commonly-assigned U.S. Pat. No. 6,734,401 titled ENHANCED SAMPLE PROCESSING DEVICES SYSTEMS AND METHODS (Bedingham et al.) and U.S. Patent Application Publication No. US 2002/0064885 titled SAMPLE PROCESSING DEVICES. Other useable device constructions may be found in, e.g., U.S. Provisional Patent Application Ser. No. 60/214,508 filed on Jun. 28, 2000 and entitled THERMAL PROCESSING DEVICES AND METHODS; U.S. Provisional Patent Application Ser. No. 60/214,642 filed on Jun. 28, 2000 and entitled SAMPLE PROCESSING DEVICES, SYSTEMS AND METHODS; U.S. Provisional Patent Application Ser. No. 60/237,072 filed on Oct. 2, 2000 and entitled SAMPLE PROCESSING DEVICES, SYSTEMS AND METHODS; U.S. Provisional Patent Application Ser. No. 60/260,063 filed on Jan. 6, 2001 and titled SAMPLE PROCESSING DEVICES, SYSTEMS AND METHODS; U.S. Provisional Patent Application Ser. No. 60/284,637 filed on Apr. 18, 2001 and titled ENHANCED SAMPLE PROCESSING DEVICES, SYSTEMS AND METHODS; and U.S. Patent Application Publication No. US 2002/0048533 titled SAMPLE PROCESSING DEVICES AND CARRIERS. Other potential device constructions may be found in, e.g., U.S. Pat. No. 6,627,159 titled CENTRIFUGAL FILLING OF SAMPLE PROCESSING DEVICES (Bedingham et al.).

Although relative positional terms such as "top", "bottom", "above", "below", etc. may be used in connection with the present invention, it should be understood that those terms are used in their relative sense only. For example, when used in connection with the apparatus of the present invention, "top" and "bottom" may be used to signify opposing major sides of the apparatus and their modules. In actual use, elements described as "top" or "bottom" may be found in any orientation or location and should not be considered as limiting the apparatus and methods to any particular orientation or location. For example, the top surface of the sample processing apparatus or module may actually be located below the bottom surface of the sample processing apparatus or module during processing (although the top surface would still be found on the opposite side of the sample processing apparatus or module from the bottom surface).

Figure 1:
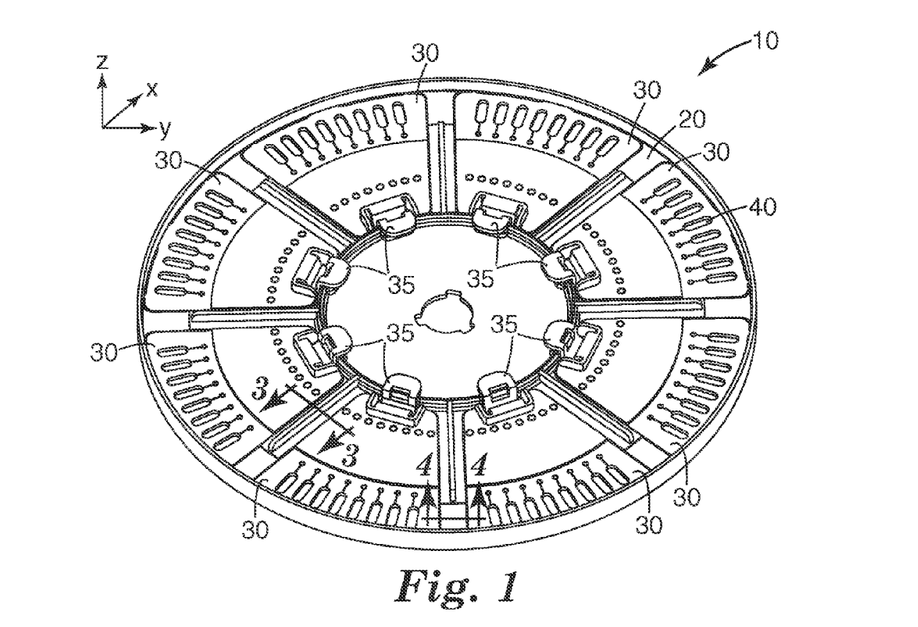
FIG. 1 is a perspective view of a top surface of an exemplary modular sample processing apparatus kit according to the present invention with the process modules loaded into the frame.

One major surface of one embodiment of a modular sample processing apparatus 10 is depicted in FIG. 1. The apparatus 10 includes a frame 20 with process modules 30 located in openings of the frame 20, i.e., the kit is in the assembled configuration. The frame 20 is shown alone in FIG. 2, where each of the openings 22 is depicted. The openings 22 are defined by a series of struts 24 that extend outward from a central core 26 to an outer support ring 28.

The apparatus 10 further includes a spindle aperture 12 located in the central core 26 of the frame. The spindle aperture 12 may preferably be sized and shaped to accept a spindle that can be used to rotate the sample processing apparatus 10 about a rotational axis that extends along the z-axis direction through the center of the spindle aperture 12.

The exact number of openings 22 in the frame 20 of any one sample processing apparatus of the present invention may vary. The depicted apparatus 10 includes eight process modules 30 in eight openings 22 in the frame 20, but the frame of an apparatus of the present invention may have as few as two openings up to as many openings as desired, i.e., more than eight openings may be provided.

Furthermore, although a process module 30 is located within each of the openings 22 in the depicted frame 20, each of the openings 22 in the frame 20 may not necessarily be populated with a process module 30. For example, some of the openings 22 may be left empty if the frame 20 and any processing system adapted to process sample materials using the apparatus 10 are designed to process an apparatus 10 in which one or more openings in the frame 20 are left empty.

Alternatively, the openings 22 in the frame that are not occupied by process modules 30 may be occupied by blank modules that, e.g., do not include any reagents and/or sample materials to be processed. As used herein, a "blank module" may include a truly blank module (i.e., a featureless body adapted to be located in an opening in the frame), a process module that is not loaded with preprinted reagents, a process module loaded with preprinted reagents but no sample materials, a used process module that is no longer needed (but is useful to fill an opening in a frame while other process modules are being processed), etc.

Blank modules may be provided if the system used to process the apparatus is designed to work best with a fully-loaded frame (such as, for example, the systems described in U.S. patent application Ser. No. 11/174,757, titled SAMPLE PROCESSING DEVICE COMPRESSION SYSTEMS AND METHODS, filed on even date herewith. Another potential reason for loading blank modules in a frame in which all of the openings are not occupied by process modules with sample materials is to balance the frame for rotational purposes, with the blank modules serving as counterweights for the process modules. In such an application, some of the openings in the frame may be left empty if no counterweight is required for a process module located on the opposite side of the frame.

Figure 2:
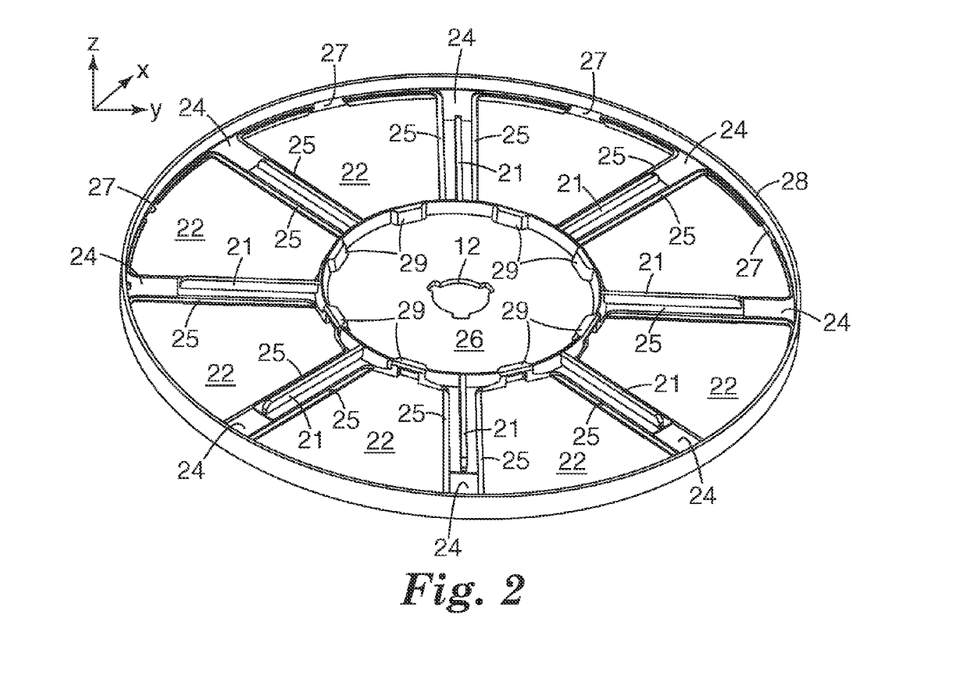
FIG. 2 is perspective view of the frame of the modular sample processing apparatus of FIG. 1 with the process modules removed.

The process modules 30 may be retained within the openings 22 in the frame 20 by any suitable technique or structures. In the depicted embodiment, the struts 24 that define the edges of the frame openings 22 include a lip 25 on which a complementary edge 31 of the process module 30 rests when the process module 30 is in opening 22 (see, e.g., FIGS. 2 and 3). It may be preferred that the lip 25 extend along the entire length of the strut 24 as seen in FIG. 2. It may be further preferred that the lip 25 extend out to and along at least a portion of the outer support ring 28 (as seen in FIG. 2).

Figure 3:
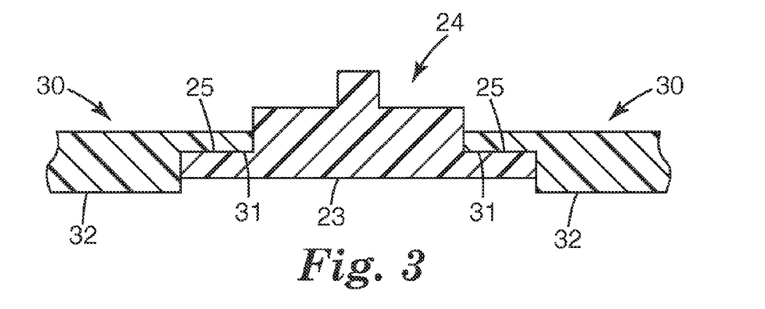
FIG. 3 is an enlarged cross-sectional view of a portion of the sample processing apparatus of FIG. 1 taken along line 3-3 in FIG. 1.

The lips 25 and edges 31 of the process modules preferably work together to support the process modules 30 within the openings 22 of the frame. As seen in FIG. 3, it may be preferred that the bottom surface 23 of the strut 24 be raised in the z-direction relative to the bottom surfaces 32 of the process modules 30. In such an arrangement, it may be easier to ensure that the bottom surfaces 32 of the process modules 30 can rest on or come into physical contact with a thermal transfer surface as will be described elsewhere herein. For example, the bottom surfaces 32 of the process modules 30 within a given frame 20 of a sample processing apparatus may preferably define a contact plane, with the surface 23 of the strut 24 located above the contact plane defined by the lowermost surfaces 32 of the process modules 30. This concept is also described in connection with FIG. 6 below.

A recess 27 located along the outer support ring 28 may also be provided to assist in retaining the process modules 30 within the openings 22. The recess 27 may preferably be adapted to receive a complementary tab 33 on the process module 30 (see, e.g., FIG. 4). The tab 33 and recess 27 may preferably assist in aligning the process module 30 within opening 22 as well as retaining the module 30 within the opening 22. In addition, while the lip 25 and edge 31 of the module 30 prevent the module 30 from moving in one direction along the z-axis, the recess 27 and complementary tab 33 may preferably mate with each other in a manner that prevents movement of the module 30 relative to the frame 20 in two directions along the z-axis.

At the opposite end of the process modules 30 from the tab 33, a clip structure 35 is preferably used to further assist in retaining the process modules 30 in the openings 22 of the frame 20. The clip structure 35 may preferably include a slot 36 that may preferably be sized and shaped to receive a complementary frame tab 29 on the edge of the opening 22 extending along the central core 26 (see FIG. 2). Similar to recesses 27 and tabs 33 on the opposite outer edges of the openings 22, the slot 36 and frame tab 29 may preferably restrict movement of the module 30 in two directions along the z-axis.

The clip structure 35 in which the slot 36 is located may preferably include a handle 37 that can be manipulated to move the slot 36 out of engagement with the frame tab 29 such that the process modules 30 can be removed from the openings 22 in the frame 20. It may be preferred that the clip structure 35 be constructed such that portion containing slot 36 be resiliently mounted to press against the frame tab 29 until the handle 37 is manipulated or forced in a direction towards the module tab 33 to release the slot 36 from engagement with the frame tab 29. The clip structure 35 may be molded of polymeric materials with the body of the process module 30 or the clip structure may be constructed of different materials (e.g., metals, etc.) from the body of the process module 30.

The frame tabs 29 and complementary slots 36 in clip structure 35 along with module tabs 33 and frame recesses 27 may preferably combine to retain the process modules 30 within openings 22 in the frame 20. Together, these features represent one exemplary embodiment of mechanical interlocking structure that can be used to retain process modules in openings 22 of the frame 20. Other variations will be known to those skilled in the art. For example, the locations of the tabs and slots/recesses may be reversed, etc.

Figure 3A:
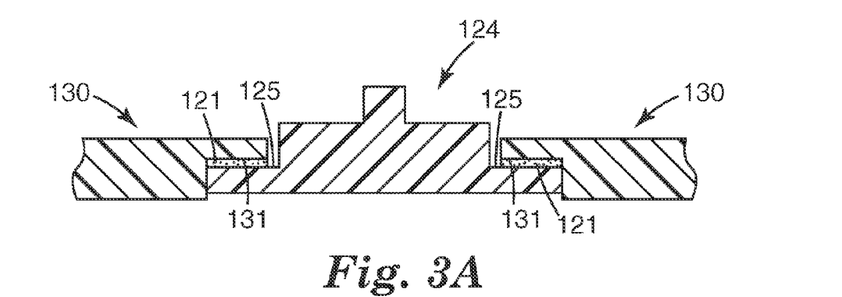
FIG. 3A is a cross-sectional view of a portion of an alternative sample processing apparatus.

It should be understood that in place of mechanical interlocking structures, alternative retention techniques may be used. One such alternative technique is depicted in FIG. 3A in which adhesive 121 is depicted between the lips 125 of the strut 124 and complementary edges 131 of the process modules 130. The adhesive 121 may preferably be a pressure sensitive adhesive that allows for non-destructive removal of the process modules 130 from a frame (not shown). In other instances, the adhesive may be permanent, i.e., adapted to permanently retain the process modules 130—with both the modules 130 and the frame (of which strut 124 is a portion) being discarded after use.

The frames used in sample processing apparatus of the present invention may be constructed of any suitable material or materials. It may, however, be preferred that the frames be constructed of materials that have relatively low thermal conductivity, e.g., it may be preferred that the frames be manufactured of polymeric materials as opposed to metallic. In some embodiments, the frames may consist essentially of polymeric materials (e.g., polycarbonates, polypropylenes, polyethylenes, etc.), although such a frame may include a metallic hub at its center that is insert-molded into a polymeric structure (if helpful for mating with, e.g., spindle, etc.).

In some instances, the frames may be designed for reuse with different process modules. In other instances, the frames may be designed for disposal after a single use. The attachment of process modules within a disposable frame may, in some instances, be permanent—i.e., require destruction of some portion of the frame and/or process module to separate the same after use. If designed for multiple uses, the frames may even, in some instances, be attached to the base plate of a processing system such as those described in, e.g., U.S. Pat. No. 6,734,401 titled ENHANCED SAMPLE PROCESSING DEVICES SYSTEMS AND METHODS (Bedingham et al.) or U.S. patent application Ser. No. 11/174,757, titled SAMPLE PROCESSING DEVICE COMPRESSION SYSTEMS AND METHODS, filed on even date herewith.

As discussed herein, each of the process modules used in sample processing apparatus of the present invention preferably include process chambers that are adapted to retain sample materials while one or more processes are performed on or using the sample materials. Examples of some potential processes that may be performed include, e.g., PCR, Sanger sequencing, etc.

It may be preferred that the process chambers 40 in the process modules 30 define an annular processing ring when the process modules 30 are retained in the openings 22 in the frame 20 of the sample processing apparatus 10. This concept may, perhaps, be best illustrated in the attached figures with reference to FIG. 1 where process chambers 40 are arranged in a manner that defines an annular processing ring on the apparatus.

As seen in FIG. 1, it may be preferred that the multiple process chambers 40 on each process module 30 be arranged to form a part of a circular arc although such an arrangement is not required. For example, it may be possible to arrange the process chambers 40 on any one process module 30 in a straight line, such that, in effect, the process chambers 40 would define sides of an octagonal, hexagonal, pentagonal, etc. ring. Other arrangements may also be possible.

Regardless of the precise arrangement of the process chambers 40, they are preferably within the boundaries of an annular processing ring with some variations possible within a given process module or from module to module within a given sample processing apparatus. In another variation, it should be understood that in some embodiments, not all openings 22 in the frame 20 will be populated by a process module 30 that includes process chambers 40. As used in connection with the present invention, it may be sufficient that one process module be provided that includes process chambers that can be used to define an annular processing ring. For example, it can be seen in FIG. 1 that one process module 30 and its associated process chambers 40 could be sufficient to define an annular processing ring in connection with the present invention.

Figure 4:
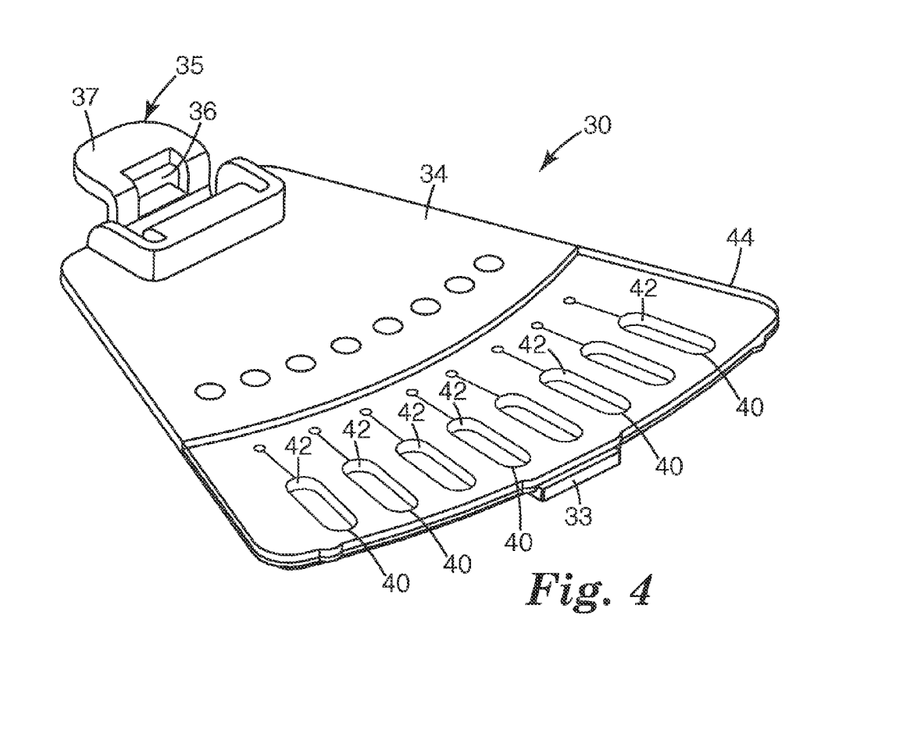
FIG. 4 is an enlarged perspective view of the top surface of one of the process modules of the apparatus of FIG. 1.
Figure 5:
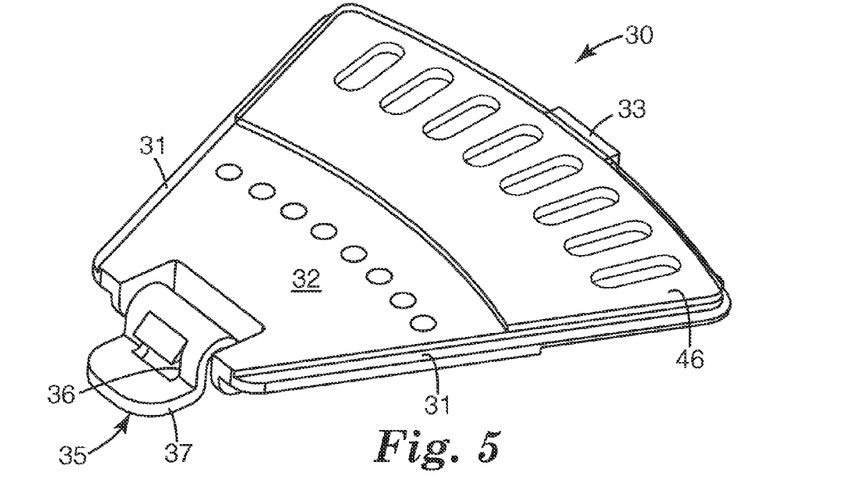
FIG. 5 is an enlarged perspective view of the bottom surface of the process module of FIG. 4.

FIGS. 4 and 5 are enlarged views of one of the process modules 30 depicted in connection with the sample processing apparatus 10 of FIG. 1. FIG. 4 is a view of the top surface 34 of the process module 30 and depicts the construction of process chambers 40 in more detail. The process chambers 40 may preferably be constructed as voids 42 formed through the top surface 34 and bottom surface 32 (see FIG. 5) of the body of the process module 30. A first cover 44 may preferably be attached the top surface 34 of the process module to define the tops of the process chambers 40. On the opposite side of the process module 30 (see FIG. 5) a second cover 46 may be attached to the bottom surface 32 to define the bottoms of the process chambers 40.

It may be preferred that the covers 44 and 46 used to define the process chambers 40 in combination with the voids 42 in the depicted embodiment of a process module 30 as seen in FIGS. 4 and 5 are limited to the generally the area of the annular process ring, they may not necessarily be so limited. For example, it may be possible that one or both of the covers 44 and 46 may extend over substantially the entire surface of the process module 30.

One potential advantage of the multiple covers 44 and 46 attached to the surfaces 32 and 34 of the process module 30 is that covers 44 and 46 may be constructed of different materials that provide different properties. It may be preferred that at least one of the covers 44 and 46 defining the process chambers 40 be constructed of a material or materials that substantially transmit electromagnetic energy of selected wavelengths. For example, it may be preferred that one of the covers 44 and 46 be constructed of a material that allows for visual or machine monitoring of fluorescence or color changes within the process chambers 40, the delivery of electromagnetic energy into the process chambers, etc.

It may also be preferred that at least one of the covers 44 and 46 include a metallic layer, e.g., a metallic foil. If provided as a metallic foil, the cover may preferably include a passivation layer on the surface that faces the interior of the fluid structures to prevent contact between the sample materials and the metal. Such a passivation layer may also function as a bonding structure where it can be used in, e.g., hot melt bonding of polymers. As an alternative to a separate passivation layer, any adhesive layer used to attach the cover to the process module 30 may also serve as a passivation layer to prevent contact between the sample materials and any metals in the cover.

In the illustrative embodiment of the process module depicted in FIGS. 4 and 5, the first cover 44 may preferably be manufactured of a polymeric film (e.g., polypropylene, polyester, polyethylene, etc.) while the cover 46 on the opposite side of the process module 30 may preferably include a metallic layer (e.g., a metallic foil layer of aluminum, etc.). In such an embodiment, the first cover 44 preferably transmits electromagnetic radiation of selected wavelengths, e.g., the visible spectrum, the ultraviolet spectrum, etc. into and/or out of the process chambers 40 while the metallic layer of the second cover 46 facilitates thermal energy transfer into and/or out of the process chambers 40 using thermal structures/surfaces as described in, e.g., U.S. Pat. No. 6,734,401 titled ENHANCED SAMPLE PROCESSING DEVICES SYSTEMS AND METHODS (Bedingham et al.) or U.S. patent application Ser. No. 11/174,757, titled SAMPLE PROCESSING DEVICE COMPRESSION SYSTEMS AND METHODS, filed on even date herewith.

It may be preferred that, where the second cover 46 is selected for its thermal conductivity, the size of the second cover be limited such that it generally corresponds to the area of the annular processing ring defined by the process chambers 40. A potential benefit of limiting the size of a thermally conductive cover is that the amount of thermal energy transferred to areas other than the annular process ring may be limited. As such, the transfer of thermal energy to areas that are not occupied by process chambers may be limited. In contrast, although the first cover 44 is also depicted as being generally limited to the area of the annular processing ring, it could alternatively extend further without significantly degrading performance of the process module in a thermal process.

Although some examples of materials for the covers are described above, it should be understood that the body of the process module and any covers attached thereto may be manufactured of any suitable material or materials. Examples of suitable materials may include, e.g., polymeric materials (e.g., polypropylene, polyester, polycarbonate, polyethylene, etc.), metals (e.g., metal foils), etc. The covers may preferably, but not necessarily, be provided in generally flat sheet-like pieces of, e.g., metal foil, polymeric material, multi-layer composite, etc. It may be preferred that the materials selected for the body and the covers of the disks exhibit good water barrier properties.

Figure 6:
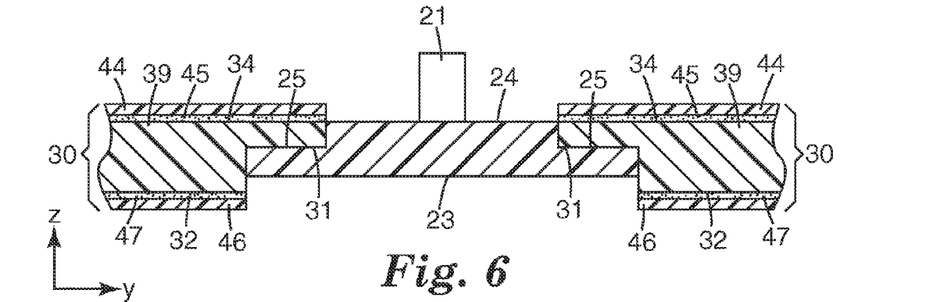
FIG. 6 is an enlarged cross-sectional view of a portion of the sample processing apparatus of FIG. 1 taken along line 3-3 in FIG. 1.

The covers 44 and 46 may be attached to the surfaces 32 and 34 of the process module 30 by any suitable technique or techniques, e.g., melt bonding, adhesives, combinations of melt bonding and adhesives, etc. If melt bonded, it may be preferred that both the cover and the surface to which it is attached include, e.g., polypropylene or some other melt bondable material, to facilitate melt bonding. It may, however, be preferred that the covers be attached using pressure sensitive adhesive. The pressure sensitive adhesive may be provided in the form of a layer of pressure sensitive adhesive that may preferably be provided as a continuous, unbroken layer 45 or 47 between the cover 44 or 46 and the opposing surface 32 or 34 or body 39 as seen in FIG. 6. Examples of some potentially suitable attachment techniques, adhesives, etc. may be described in, e.g., U.S. Pat. No. 6,734,401 titled ENHANCED SAMPLE PROCESSING DEVICES SYSTEMS AND METHODS (Bedingham et al.) and U.S. Patent Application Publication No. US 2002/0064885 titled SAMPLE PROCESSING DEVICES (Bedingham et al.).

Pressure sensitive adhesives typically exhibit viscoelastic properties that may preferably allow for some movement of the covers relative to the underlying body to which the covers are attached. The movement may be the result of deformation of the annular processing ring to, e.g., conform to the shape of a thermal transfer structure as described in U.S. patent application Ser. No. 11/174,757, titled SAMPLE PROCESSING DEVICE COMPRESSION SYSTEMS AND METHODS, filed on even date herewith and in U.S. patent application Ser. No. 11/174,680, titled COMPLIANT MICROFLUIDIC SAMPLE PROCESSING DISKS, filed on even date herewith. In sample processing apparatus of the present invention, portions of the process modules and the frames may both be deformed in response to compressive forces.

The relative movement may also be the result of different thermal expansion rates between the covers and the body. Regardless of the cause of the relative movement between covers and bodies in the process modules of the present invention, it may be preferred that the viscoelastic properties of the pressure sensitive adhesive allow the process chambers (and other fluid features of any fluid structures—if present) to preferably retain their fluidic integrity (i.e., they do not leak) in spite of the deformation.

Many different pressure sensitive adhesives may potentially be used in connection with the present invention. One well-known technique for identifying pressure sensitive adhesives is the Dahlquist criterion. This criterion defines a pressure sensitive adhesive as an adhesive having a 1 second creep compliance of greater than $1 \times 10^{-6}$ cm$^2$/dyne as described in *Handbook of Pressure Sensitive Adhesive Technology*, Donatas Satas (Ed.), 2$^{nd}$ Edition, p. 172, Van Nostrand Reinhold, New York, N.Y., 1989. Alternatively, since modulus is, to a first approximation, the inverse of creep compliance, pressure sensitive adhesives may be defined as adhesives having a Young's modulus of less than $1 \times 10^{6}$ dynes/cm$^2$. Another well known technique for identifying a pressure sensitive adhesive is that it is aggressively and permanently tacky at room temperature and firmly adheres to a variety of dissimilar surfaces upon mere contact without the need of more than finger or hand pressure, and which may be removed from smooth surfaces without leaving a residue as described in *Test Methods for Pressure Sensitive Adhesive Tapes*, Pressure Sensitive Tape Council, (1996). Another suitable definition of a suitable pressure sensitive adhesive is that it preferably has a room temperature storage modulus within the area defined by the following points as plotted on a graph of modulus versus frequency at 25° C.: a range of moduli from approximately $2 \times 10^5$ to $4 \times 10^5$ dynes/cm$^2$ at a frequency of approximately 0.1 radian/second (0.017 Hz), and a range of moduli from approximately $2 \times 10^6$ to $8 \times 10^6$ dynes/cm$^2$ at a frequency of approximately 100 radians/second (17 Hz) (for example see FIG. 8-16 on p. 173 of *Handbook of Pressure Sensitive Adhesive Technology*, Donatas Satas (Ed.), 2$^{nd}$ Edition, Van Nostrand Rheinhold, New York, 1989). Any of these methods of identifying a pressure sensitive adhesive may be used to identify potentially suitable pressure sensitive adhesives for use in the methods of the present invention.

It may be preferred that the pressure sensitive adhesives used in connection with the sample processing apparatus of the present invention include materials which ensure that the properties of the pressure sensitive adhesive are not adversely affected by water. For example, the pressure sensitive adhesive will preferably not lose adhesion, lose cohesive strength, soften, swell, or opacify in response to exposure to water during sample loading and processing. Also, the pressure sensitive adhesives preferably do not contain any components which may be extracted into water during sample processing, thus possibly compromising performance.

In view of these considerations, it may be preferred that the pressure sensitive adhesive be composed of hydrophobic materials. As such, it may be preferred that the pressure sensitive adhesive be composed of silicone materials. That is, the pressure sensitive adhesive may be selected from the class of silicone pressure sensitive adhesive materials, based on the combination of silicone polymers and tackifying resins, as described in, for example, "Silicone Pressure Sensitive Adhesives", *Handbook of Pressure Sensitive Adhesive Technology*, 3$^{rd}$ Edition, pp. 508-517. Silicone pressure sensitive adhesives are known for their hydrophobicity, their ability to withstand high temperatures, and their ability to bond to a variety of dissimilar surfaces.

The composition of the pressure sensitive adhesives is preferably chosen to meet the stringent requirements of the present invention. Some suitable compositions may be described in International Publication WO 00/68336 titled SILICONE ADHESIVES, ARTICLES, AND METHODS (Ko et al.).

Other suitable compositions may be based on the family of silicone-polyurea based pressure sensitive adhesives. Such compositions are described in U.S. Pat. No. 5,461,134 (Leir et al.); U.S. Pat. No. 6,007,914 (Joseph et al.); International Publication No. WO 96/35458 (and its related U.S. patent application Ser. No. 08/427,788 (filed Apr. 25, 1995); Ser. No. 08/428,934 (filed Apr. 25, 1995); Ser. No. 08/588,157 (filed Jan. 17, 1996); and Ser. No. 08/588,159 (filed Jan. 17, 1996); International Publication No. WO 96/34028 (and its related U.S. patent application Ser. No. 08/428,299 (filed Apr. 25, 1995); Ser. No. 08/428,936 (filed Apr. 25, 1995); Ser. No. 08/569,909 (filed Dec. 8, 1995); and Ser. No. 08/569,877 (filed Dec. 8, 1995)); and International Publication No. WO 96/34029 (and its related U.S. patent application Ser. No. 08/428,735 (filed Apr. 25, 1995) and Ser. No. 08/591,205 (filed Jan. 17, 1996)).

Such pressure sensitive adhesives are based on the combination of silicone-polyurea polymers and tackifying agents. Tackifying agents can be chosen from within the categories of functional (reactive) and nonfunctional tackifiers as desired. The level of tackifying agent or agents can be varied as desired so as to impart the desired tackiness to the adhesive composition. For example, it may be preferred that the pressure sensitive adhesive composition be a tackified polydiorganosiloxane oligurea segmented copolymer including (a) soft polydiorganosiloxane units, hard polyisocyanate residue units, wherein the polyisocyanate residue is the polyisocyanate minus the —NCO groups, optionally, soft and/or hard organic polyamine units, wherein the residues of isocyanate units and amine units are connected by urea linkages; and (b) one or more tackifying agents (e.g., silicate resins, etc.).

Furthermore, the pressure sensitive adhesive layers used in connection with the invention can be a single pressure sensitive adhesive or a combination or blend of two or more pressure sensitive adhesives. The pressure sensitive layers may result from solvent coating, screen printing, roller printing, melt extrusion coating, melt spraying, stripe coating, or laminating processes, for example. An adhesive layer can have a wide variety of thicknesses as long as it meets exhibits the above characteristics and properties. In order to achieve maximum bond fidelity and, if desired, to serve as a passivation layer, the adhesive layer may preferably be continuous and free from pinholes or porosity.

Even though the sample processing devices may be manufactured with a pressure sensitive adhesive to connect the various components, e.g., covers, bodies, etc., together, it may be preferable to increase adhesion between the components by laminating them together under elevated heat and/or pressure to ensure firm attachment of the components.

It may be preferred to use adhesives that exhibit pressure sensitive properties. Such adhesives may be more amenable to high volume production of sample processing devices since they typically do not involve the high temperature bonding processes used in melt bonding, nor do they present the handling problems inherent in use of liquid adhesives, solvent bonding, ultrasonic bonding, and the like.

The adhesives are preferably selected for their ability to, e.g., adhere well to materials used to construct the covers and bodies to which the covers are attached, maintain adhesion during high and low temperature storage (e.g., about −80° C. to about 150° C.) while providing an effective barrier to sample evaporation, resist dissolution in water, react with the components of the sample materials used in the disks, etc. Thus, the type of adhesive may not be critical as long as it does not interfere (e.g., bind DNA, dissolve, etc.) with any processes performed in the sample processing apparatus 10. Preferred adhesives may include those typically used on cover films of analytical devices in which biological reactions are carried out. These include poly-alpha olefins and silicones, for example, as described in International Publication Nos. WO 00/45180 (Ko et al.) and WO 00/68336 (Ko et al.).

Furthermore, the pressure sensitive adhesive layer of the sample processing disks of the present invention can be a single adhesive or a combination or blend of two or more adhesives. The adhesive layers may result from solvent coating, screen printing, roller printing, melt extrusion coating, melt spraying, stripe coating, or laminating processes, for example. An adhesive layer can have a wide variety of thicknesses as long as it meets exhibits the above characteristics and properties. In order to achieve maximum bond fidelity and, if desired, to serve as a passivation layer, the adhesive layer may preferably be continuous and free from pinholes or porosity.

It may be preferred that the portions of the process modules 30 and the frame 20 located within the annular processing ring exhibit sufficient compliance such that the components within the annular processing ring can conform to the shape of an underlying thermal transfer surface under pressure. Compliance is preferably achieved with some deformation of the components in annular processing ring while maintaining the fluidic integrity of the process chambers 40 (i.e., without causing leaks). Such a compliant annular processing ring may be useful when used in connection with the methods and systems described in, e.g., U.S. patent application Ser. No. 11/174,757, titled SAMPLE PROCESSING DEVICE COMPRESSION SYSTEMS AND METHODS, filed on even date herewith.

FIG. 6 is an enlarged cross-sectional view of the sample processing apparatus of FIG. 1 taken along line 6-6 in FIG. 1 and can be used to discuss some of the features that may contribute to compliance and thermal transfer into and/or out of the process chambers.

As depicted in FIGS. 2 and 6, compliance of the annular processing ring may be enhanced by limiting the amount of frame material located within the annular processing ring. For example, the struts 24 may include ribs 21 that extend outward from the central core 26, but that terminate short of the annular processing ring as seen in FIGS. 2 and 6.

In addition, compliance of the of the process modules 30 within the frame 20 may also be enhanced by providing the process modules 30 with a composite thickness that is greater than the thickness of the strut 24 within the annular processing ring (where thickness is measured along the z-axis). As discussed herein, limiting the thickness of the strut 24 within the annular processing ring may also provide an advantage in that the cover 46 becomes the lowest component of the sample processing apparatus. For example, the covers 46 of the process modules 30 within a given frame 20 of a sample processing apparatus may preferably define a contact plane, with the surface 23 of the strut 24 located above the contact plane defined by the lowermost surface of the covers 46.

Although composite structures for the process modules formed using viscoelastic pressure sensitive adhesives to attach covers to the process module bodies may be useful to provide compliance of the annular processing rings containing the process chambers, further enhancement in the compliance of the annular processing rings may be achieved by forming the process chambers using voids formed through the process module body. In some embodiments, it may be preferred that the voids of the process chambers 40 occupy 50% or more of the volume of the process module body located within the annular processing ring defined by the process chambers 40.

Referring to the apparatus of FIG. 1, no structure is provided to supply materials in the process chambers 40. It may be preferred in such an embodiment that reagents be located in the process chambers 40 during manufacturing of the process modules 30. Sample materials can then be delivered into the process chambers 40 by, e.g., piercing one of the covers 44 and 46, by attaching one of the covers after loading the process chambers with sample material, etc. U.S. Patent Application Publication No. 2003/0118804, titled SAMPLE PROCESSING DEVICE WITH RESEALABLE PROCESS CHAMBER, published Jun. 26, 2003 (Bedingham et al.) describes resealable process chambers that can be loaded by piercing a resealable cover.

In other embodiments, however, it may be preferred to provide fluid structures that include features such as, e.g., input wells, delivery channels, loading chambers, multiple process chambers, vias, valves, filters, etc. Examples of such fluid structures (sometimes alternately referred to as process arrays) may be found in, e.g., U.S. Pat. No. 6,734,401 titled ENHANCED SAMPLE PROCESSING DEVICES SYSTEMS AND METHODS (Bedingham et al.); U.S. Patent Application Publication No. US 2002/0064885 titled SAMPLE PROCESSING DEVICES (Bedingham et al.); and U.S. patent application Ser. No. 11/174,680, titled COMPLIANT MICROFLUIDIC SAMPLE PROCESSING DISKS, filed on even date herewith.

Figure 7:
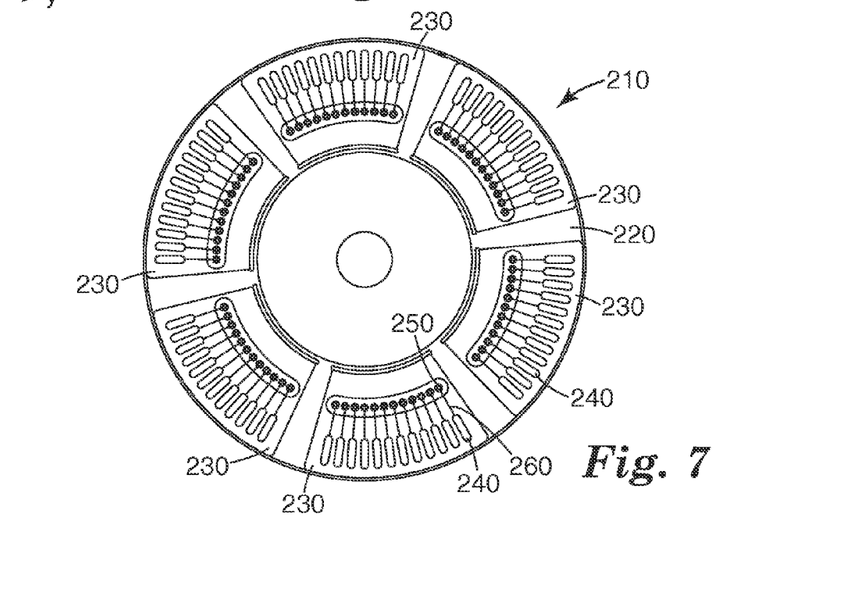
FIG. 7 depicts another exemplary modular sample processing apparatus kit according to the present invention.

FIG. 7 depicts an alternate sample processing apparatus according to the present invention in which input wells 250 are provided in addition to process chambers 240 on each of the process modules 230 provided in the sample processing apparatus 210. Each of the input wells 250 may preferably be connected to one of the process chambers 240 through a delivery channel 260. As such, each set of input well 250, delivery channel 260, and process chamber 240 can be characterized as fluid structure or process array as described in the documents identified in the preceding paragraph.

Another variation depicted in the sample processing apparatus of FIG. 7 is in the number of process modules 210 located in the frame 220. As seen, the apparatus 210 includes only six process modules 230 as opposed to the eight modules 30 depicted in the sample processing apparatus 10 of FIG. 1.

As discussed herein, it may be preferred that the sample processing apparatus of the present invention include process chambers that define an annular processing ring that exhibits compliance to improve thermal control over materials in the process chambers of the process modules. One example of how the compliant annular processing rings may be used in connection with the invention is depicted in connection with FIG. 8. A portion of a sample processing module 330 in a frame 320 according to the present invention is depicted in FIG. 8 in contact with a shaped transfer surface 306 formed on a thermal structure 308.

Thermal structures and their transfer surfaces may be described in more detail in, e.g., U.S. patent application Ser. No. 11/174,757, titled SAMPLE PROCESSING DEVICE COMPRESSION SYSTEMS AND METHODS, filed on even date herewith. Briefly, however, the temperature of the thermal structure 308 may preferably be controlled by any suitable technique, with the transfer surface 306 facilitating transfer of thermal energy into or out of the thermal structure 308 to control the temperature of items such as process modules placed in contact with the transfer surface 306.

Where the item to be thermally controlled is a process module in a sample processing apparatus, enhancement in thermal energy transfer between the thermal structure and the module 330 may be achieved by conforming the module 330 to the shape of the transfer surface 306. Where only a portion of the process module 330, e.g., an annular processing ring, is in contact with the transfer surface 306, it may be preferred that only that portion of the module 330 be deformed such that it conforms to the shape of the transfer surface 306.

Figure 8:
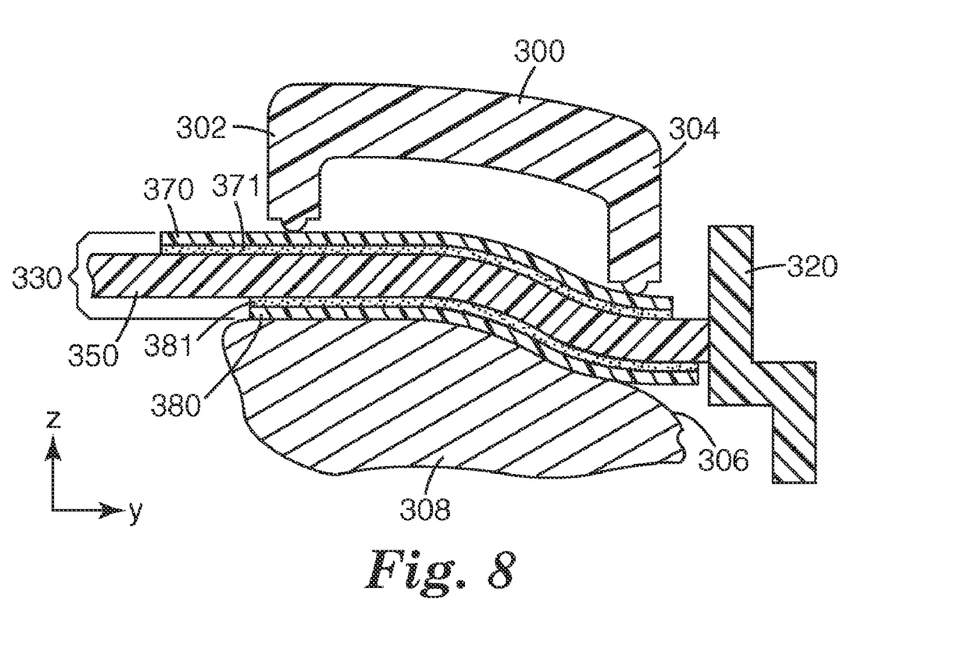
FIG. 8 depicts deformation of a portion of one sample processing apparatus according to one exemplary method of the present invention.

FIG. 8 depicts one example of such a situation in which a sample processing module 330 includes a body 350 having covers 370 and 380 attached thereto using adhesive (preferably pressure sensitive adhesive) layers 371 and 381 respectively. The covers 370 and 380 may preferably be generally limited to the area of the annular processing ring as described herein. The use of viscoelastic pressure sensitive adhesive for layers 371 and 381 may improve compliance of the annular processing ring of the process module 330 as is also described herein.

By deforming the module 330 to conform to the shape of the transfer surface 306 as depicted, thermal coupling efficiency between the thermal structure 308 and the process module 330 may be improved. Such deformation of the process module 330 may be useful in promoting contact even if the surface of the process module 330 facing the transfer surface 306 or the transfer surface 306 itself include irregularities that could otherwise interfere with uniform contact in the absence of deformation.

To further promote deformation of the process module 330 to conform to the shape of the transfer surface 306, it may be preferred to include compression rings 302 and 304 in a cover 300 used to provide a compressive force on the process module 330 in connection with the transfer surface 306, such that the rings 302 and 304 contact the process module 330—essentially spanning the annular processing ring of the process module 330 that faces the transfer surface 306. By limiting contact between the cover 300 and the annular processing ring of the module 330 to rings 302 and 304, enhanced thermal control may be achieved because less thermal energy will be transferred through the limited contact area between the cover 300 and the process module 330.

As seen in FIG. 8, deformation of the process module 330 may preferably involve deflection of the annular processing in a direction normal to the major surfaces of the process module 330, i.e., along the z-axis as depicted in FIG. 8 which can also be described as in a direction normal to the major surface of the process module 330.

In addition to deflection or deformation of the annular processing ring portion of the process module 330, it may also be preferred that the portion or portions of the frame 320 spanning the annular processing ring also be deformed by the compressive forces that deform the process module 330. It may be preferred that the frame deformation be primarily elastic deformation, i.e., that after removal of the deformation force, the frame substantially return to its pre-deformation shape. Limited deformation of the frame 320 within the area of the annular processing ring may be enhanced by terminating the reinforcing ribs (see, e.g., see reference no. 21 in FIG. 2) such that they do not extend into the annular processing ring where they could limit deformation of the frame and the process modules located therein.

As used herein and in the appended claims, the singular forms "a," "and," and "the" include plural referents unless the context clearly dictates otherwise. Thus, for example, reference to "a" or "the" component may include one or more of the components and equivalents thereof known to those skilled in the art.

All references and publications cited herein are expressly incorporated herein by reference in their entirety into this disclosure. Exemplary embodiments of this invention are discussed and reference has been made to some possible variations within the scope of this invention. These and other variations and modifications in the invention will be apparent to those skilled in the art without departing from the scope of the invention, and it should be understood that this invention is not limited to the exemplary embodiments set forth herein. Accordingly, the invention is to be limited only by the claims provided below and equivalents thereof.

The invention claimed is:

1. A modular sample processing apparatus kit comprising:
   a frame comprising a plurality of openings arranged in an annular array around a center of the frame;
   one or more process modules adapted to be retained within one opening of the plurality of openings of the frame, wherein adjacent process modules loaded into adjacent openings are separated from each other by a radial strut of the frame, and wherein each process module comprises:
      a module body comprising first and second major surfaces;
      a fluid structure in the process module, the fluid structure comprising a process chamber,
      wherein the process chamber comprises a volume defined by a void formed in the module body;
   wherein the process chambers of the one or more process modules define an annular processing ring of the modular sample processing apparatus when the one or more process modules are retained within the plurality of openings of the frame;
   and wherein each process module further comprises a z-axis thickness measured in a direction normal to the first and second major surfaces of the module body that is larger than a z-axis thickness of the portion of each radial strut of the frame located within the annular processing ring.

2. A kit according to claim 1 wherein, for each of the process modules, the process chambers occupy 50% or more of the volume of the portion of the module body within the annular processing ring.

3. A kit according to claim 1, wherein each process module comprises a mechanical interlocking structure that mates with a complementary structure in each opening of the plurality of openings of the frame.

4. A kit according to claim 1, wherein each process module is adhesively retained in each opening of the plurality of openings of the frame.

5. A kit according to claim 1, wherein the process chamber in each process module comprises a window that transmits electromagnetic energy of selected wavelengths into or out of the process chamber.

6. A kit according to claim 1, wherein the process chamber in each process module of the one or more process modules contains a reagent, and wherein the reagents in the process chambers of at least two process modules are different.

7. A modular sample processing apparatus kit comprising:
a frame comprising at least one opening;
at least one process module adapted to be retained within the at least one opening of the frame, wherein the at least one process module comprises:
a module body comprising first and second major surfaces;
a fluid structure in the process module, the fluid structure comprising an input well in fluid communication with a process chamber, wherein the input well is located radially inward of the process chamber relative to the center of the frame,
wherein the process chamber comprises a volume defined by a void formed in the module body;
and wherein the at least one process module further comprises a z-axis thickness measured in a direction normal to the first and second major surfaces of the module body that is larger than a z-axis thickness of a portion of the frame.

8. A kit according to claim 7, further comprising at least one blank module adapted to be retained within the at least one opening of the frame, wherein the at least one blank module is substantially free of reagents.

9. A kit according to claim 7, wherein the at least one process module comprises a mechanical interlocking structure that mates with a complementary structure in the at least one opening of the frame.

10. A kit according to claim 7, wherein the at least one process module is adhesively retained in the at least one opening of the frame.

11. A kit according to claim 7, wherein the process chamber in the at least one process module comprises a window that transmits electromagnetic energy of selected wavelengths into or out of the at least one process chamber.

12. A kit according to claim 7, wherein the process chamber in at least one of the at least one process module contains a reagent.

13. A process module adapted for use in a modular sample processing apparatus that includes a frame with at least one opening, wherein the process module comprises:
a module body comprising first and second major surfaces;
a metallic foil layer attached to the second major surface of the module body;
a fluid structure in the process module, the fluid structure comprising a process chamber,
wherein the process chamber comprises a volume defined by a void formed through the first and second major surfaces of the module body and the metallic foil layer attached to the second major surface over the void in the second major surface;
wherein the process module comprises a z-axis thickness measured in a direction normal to the first and second major surfaces of the module body that is larger than a z-axis thickness of a portion of the frame.

14. A process module according to claim 13, wherein the metallic foil layer is attached to the second major surface of the process module with a pressure sensitive adhesive.

15. A process module according to claim 13, wherein the process module comprises a mechanical interlocking structure that mates with a complementary structure in the at least one opening of the frame.

16. A process module according to claim 13, wherein the process module is adhesively retained in the at least one opening of the frame.

17. A process module according to claim 13, wherein the process chamber comprises a window that transmits electromagnetic energy of selected wavelengths into or out of the process chamber.

18. A method of processing sample materials, the method comprising:
providing a modular sample processing apparatus comprising a frame that comprises at least one opening and at least one process module adapted to be retained within the at least one opening of the frame, wherein the at least one process module comprises a module body comprising at least one process chamber that comprises a volume defined by a void formed in the module body;
providing sample material in the at least one process chamber of the at least one process module;
deforming the sample processing apparatus on a convex transfer surface of a thermal structure, wherein a portion of the at least one process module and the frame are deflected to conform to the convex transfer surface; and
rotating the sample processing apparatus about an axis of rotation while deforming the sample processing apparatus on the convex transfer surface.

19. A method of processing sample materials, the method comprising:
providing a modular sample processing apparatus comprising a frame that comprises a plurality of openings arranged in an array and one or more process modules adapted to be retained within one opening of the plurality of openings of the frame, wherein adjacent process modules loaded into adjacent openings are separated from each other by a strut of the frame, wherein each process module further comprises a module body comprising first and second major surfaces, a metallic foil layer attached to the second major surface of the module body, at least one process chamber that comprises a volume defined by a void formed through the first and second major surfaces of the module body and the metallic foil layer attached to the second major surface over the void in the second major surface;
providing sample material in the at least one process chamber of the one or more process modules;
deforming the sample processing apparatus on a convex transfer surface of a thermal structure, wherein a portion of the one or more process modules and the frame are deflected to conform to the convex transfer surface; and
rotating the sample processing apparatus about an axis of rotation while deforming the sample processing apparatus on the convex transfer surface.

20. A method of processing sample materials, the method comprising:
providing a modular sample processing apparatus comprising a frame that comprises a plurality of openings arranged in an annular array around a center of the frame and one or more process modules adapted to be retained within one opening of the plurality of openings of the frame, wherein adjacent process modules loaded into adjacent openings are separated from each other by a radial strut of the frame, wherein each process module further comprises a module body comprising at least one process chamber that comprises a volume defined by a void formed in the module body, wherein the process chambers of the one or more process modules define an annular processing ring of the modular sample processing apparatus when the one or more process modules are retained within the plurality of openings of the frame;
providing sample material in the at least one process chamber of the one or more process modules;

deforming the annular processing ring of the sample processing apparatus on a convex transfer surface of a thermal structure, wherein a portion of the one or more process modules and the frame are deflected to conform to the convex transfer surface; and rotating the sample processing apparatus about an axis of rotation while deforming the annular processing ring on the convex transfer surface.

21. A method of processing sample materials, the method comprising:

providing a modular sample processing apparatus comprising a frame that comprises a plurality of openings arranged in an array and one or more process modules adapted to be retained within one opening of the plurality of openings of the frame, wherein adjacent process modules loaded into adjacent openings are separated from each other by a strut of the frame, wherein each process module further comprises a module body comprising first and second major surfaces, a metallic foil layer attached to the second major surface of the module body, at least one process chamber that comprises a volume defined by a void formed through the first and second major surfaces of the module body and the metallic foil layer attached to the second major surface over the void in the second major surface;

providing sample material in the at least one process chamber of the one or more process modules;

deforming the sample processing apparatus on a transfer surface of a thermal structure, wherein a portion of the one or more process modules and the frame are deflected to conform to the transfer surface; and rotating the sample processing apparatus about an axis of rotation while deforming the sample processing apparatus on the transfer surface.

22. A method of processing sample materials, the method comprising:

providing a modular sample processing apparatus comprising a frame that comprises at least one opening and at least one process module adapted to be retained within the at least one opening of the frame, wherein the at least one process module comprises a module body comprising at least one process chamber that comprises a volume defined by a void formed in the module body;

providing sample material in the at least one process chamber of the at least one process module;

deforming the sample processing apparatus on a transfer surface of a thermal structure, wherein a portion of the at least one process module and the frame are deflected to conform to the transfer surface; and rotating the sample processing apparatus about an axis of rotation while deforming the sample processing device on the transfer surface.

* * * * *

UNITED STATES PATENT AND TRADEMARK OFFICE
CERTIFICATE OF CORRECTION

PATENT NO. : 7,767,937 B2
APPLICATION NO. : 11/930628
DATED : August 3, 2010
INVENTOR(S) : William Bedingham et al.

It is certified that error appears in the above-identified patent and that said Letters Patent is hereby corrected as shown below:

Cover Page, item (54), Column 1 (Title)
Line 1, After "PROCESSING" insert -- APPARATUS, --.

Page 4, Column 2 (Other Publications)
Line 9, Delete "Minature;" and insert -- Miniature; --, therefor.

Column 1
Line 1, After "PROCESSING" insert -- APPARATUS, --.
Line 9, Delete "Allowed," and insert -- allowed, --, therefor.

Column 2
Line 9, After "such" insert -- , --.
Line 9, Before "such" delete "(".

Column 11
Line 48, Delete "Rheinhold" and insert -- Reinhold --, therefor.

Column 12
Line 39, Delete "oligurea" and insert -- oliguria --, therefor.

Signed and Sealed this

Fifth Day of October, 2010

David J. Kappos
*Director of the United States Patent and Trademark Office*